(12) United States Patent
Brown

(10) Patent No.: US 10,743,991 B2
(45) Date of Patent: Aug. 18, 2020

(54) CHORDAE TENDINEAE ADJUSTMENT

(71) Applicant: Edwards Lifesciences Corporation, Irvine, CA (US)

(72) Inventor: Oliver Brown, Berlin (DE)

(73) Assignee: Edwards Lifesciences Corporation, Irvine, CA (US)

( * ) Notice: Subject to any disclaimer, the term of this patent is extended or adjusted under 35 U.S.C. 154(b) by 109 days.

(21) Appl. No.: 15/845,539

(22) Filed: Dec. 18, 2017

(65) Prior Publication Data

US 2018/0206992 A1     Jul. 26, 2018

Related U.S. Application Data

(60) Provisional application No. 62/449,419, filed on Jan. 23, 2017.

(51) Int. Cl.
| | |
|---|---|
| *A61F 2/24* | (2006.01) |
| *A61B 17/12* | (2006.01) |
| *A61B 17/122* | (2006.01) |
| *A61B 17/04* | (2006.01) |
| *A61B 17/00* | (2006.01) |

(52) U.S. Cl.
CPC .......... *A61F 2/2457* (2013.01); *A61B 17/122* (2013.01); *A61B 17/12013* (2013.01); *A61F 2/2427* (2013.01); *A61F 2/2466* (2013.01); *A61B 17/0469* (2013.01);
(Continued)

(58) Field of Classification Search
CPC .... A61F 2/2442; A61F 2/2454; A61F 2/2457; A61F 2/246; A61F 2/2427; A61F 2/243; A61F 2/2433; A61F 2/2436; A61F 2/2439; A61F 2/00243; A61B 2017/00243;
(Continued)

(56) References Cited

U.S. PATENT DOCUMENTS

| | | |
|---|---|---|
| 7,608,091 B2 | 10/2009 | Goldfarb et al. |
| 8,968,393 B2 | 3/2015 | Rothstein |

(Continued)

OTHER PUBLICATIONS

Nielsen SL, "Mechanism of incomplete mitral leaflet coaptation—interaction of chordal restraint and changes in mitral leaflet coaptation geometry. Insight from in vitro validation of the premise of force equilibrium." J Bimech Eng. Oct. 2002; 124(5): 596-608.

*Primary Examiner* — Tan-Uyen T Ho
*Assistant Examiner* — Chima U Igboko
(74) *Attorney, Agent, or Firm* — Chang & Hale LLP; Alan Hale

(57) ABSTRACT

A method for improving leaflet prolapse and/or valve regurgitation associated with a heart valve involves introducing a chordae tendineae capturing device into a ventricle of a heart, the chordae tendineae capturing device comprising a central hub component and a plurality of spokes, extending the plurality of spokes outward from the central hub component, rotating the chordae tendineae capturing device in a first direction to bring at least one of the plurality of spokes into physical contact with one or more cords of chordae tendineae disposed in the ventricle, further rotating the chordae tendineae capturing device in the first direction to bring the one or more cords inward towards the central hub component, and closing the plurality of spokes at least partially over the one or more cords to secure the one or more cords.

12 Claims, 8 Drawing Sheets

(52) U.S. Cl.
CPC ............ *A61B 2017/00243* (2013.01); *A61B 2017/00292* (2013.01); *A61B 2017/00867* (2013.01)

(58) Field of Classification Search
CPC ........... A61B 2017/00238; A61B 2017/00358; A61B 2017/00867
See application file for complete search history.

(56) References Cited

U.S. PATENT DOCUMENTS

| | | | |
|---|---|---|---|
| 2006/0095025 A1* | 5/2006 | Levine | A61B 17/00234 606/15 |
| 2007/0100439 A1 | 5/2007 | Cangialosi et al. | |
| 2007/0255396 A1 | 11/2007 | Douk et al. | |
| 2010/0298929 A1 | 11/2010 | Thornton et al. | |
| 2013/0006352 A1* | 1/2013 | Yaron | A61F 2/2445 623/2.37 |
| 2015/0039080 A1 | 2/2015 | Figulla et al. | |
| 2015/0127093 A1* | 5/2015 | Hosmer | A61F 2/2418 623/2.11 |
| 2015/0359628 A1 | 12/2015 | Keranen | |
| 2015/0359632 A1* | 12/2015 | Navia | A61F 2/2454 623/2.36 |
| 2016/0256276 A1 | 9/2016 | Yaron | |

\* cited by examiner

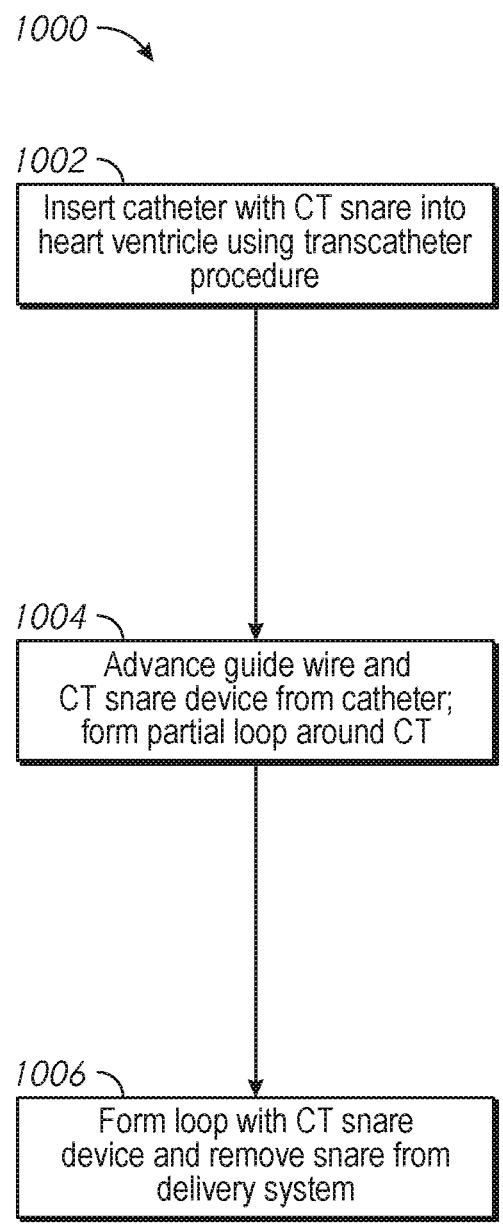
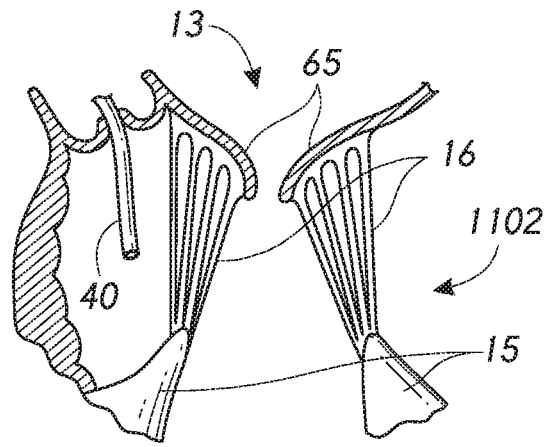
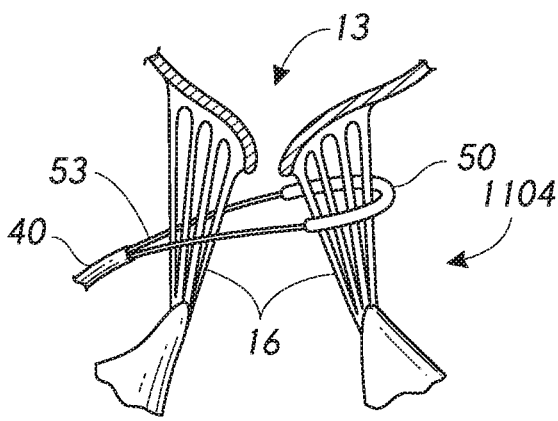
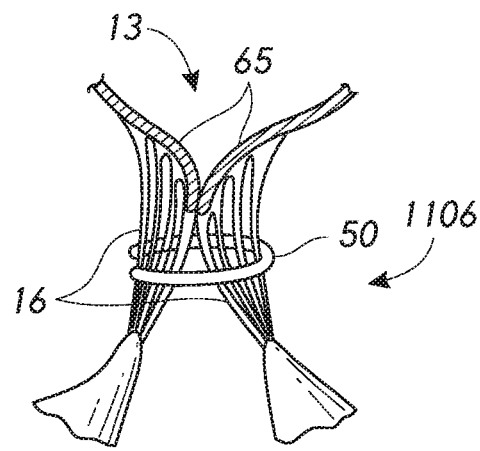
FIG. 10
FIG. 11

CHORDAE TENDINEAE ADJUSTMENT

BACKGROUND

Field

The present disclosure generally relates to the field of heart valve correction.

Description of Related Art

Heart valve dysfunction can result in regurgitation and other complications due to valve prolapse from failure of valve leaflets to properly coapt. For atrioventricular valves, chordae tendineae position and/or tension can affect the ability of valve leaflets to function properly.

SUMMARY

In some implementations, the present disclosure relates to a method for treating a heart valve. The method involves introducing a chordae tendineae capturing device into a ventricle of a heart, the chordae tendineae capturing device comprising a central hub component and a plurality of spokes, extending the plurality of spokes outward from the central hub component, rotating the chordae tendineae capturing device in a first direction to bring at least one of the plurality of spokes into physical contact with one or more cords of chordae tendineae disposed in the ventricle, further rotating the chordae tendineae capturing device in the first direction to bring the one or more cords inward towards the central hub component, and closing the plurality of spokes at least partially over the one or more cords to secure the one or more cords. Performing the method may improve at least one of prolapse of first and second leaflets of the heart valve and regurgitation of the heart valve.

In certain embodiments, introducing the chordae tendineae capturing device is performed using a transcatheter procedure. Extending the plurality of spokes, rotating the chordae tendineae capturing device in the first direction, further rotating the chordae tendineae capturing device in the first direction, and closing the plurality of spokes are performed using a delivery catheter. The method may further comprise releasing the chordae tendineae capturing device from the delivery catheter after said closing the plurality of spokes.

The chordae tendineae capturing device may disc-shaped. In certain embodiments, the central hub component is cylindrical in shape. The plurality of spokes can comprise first and second spokes that are offset from one another with respect to a longitudinal axis of the central hub component. The central hub component may comprise a spool, wherein the plurality of spokes are configured to be at least partially wrapped around the spool. In certain embodiments, the plurality of spokes consists of two spokes. Alternatively, the plurality of spokes may consist of four spokes. Furthermore, the plurality of spokes may comprise memory metal.

The method may further comprise, after rotating the chordae tendineae capturing device in the first direction, rotating the chordae tendineae capturing device in a second direction substantially opposite the first direction to release the one or more cords from the plurality of spokes. In certain embodiments, the method further comprises, after further rotating the chordae tendineae capturing device in the first direction, determining whether performance of the heart valve is satisfactory prior to said closing the plurality of spokes. When it is determined that the performance of the heart valve is not satisfactory, the method may further comprise rotating the chordae tendineae capturing device in a second direction substantially opposite the first direction. In certain embodiments, the method further comprises, after further rotating the chordae tendineae capturing device in the first direction, determining whether a position of the chordae tendineae is satisfactory prior to said closing the plurality of spokes. When it is determined that the position of the chordae tendineae is not satisfactory, the method may further comprise rotating the chordae tendineae capturing device in a second direction substantially opposite the first direction. In certain embodiments, the method further comprises, after said rotating the chordae tendineae capturing device in the first direction, determining whether a satisfactory number of cords have been captured by the plurality of spokes prior to said further rotating the chordae tendineae capturing device in the first direction.

In some implementations, the present disclosure relates to a chordae tendineae capturing device comprising a hub component and a plurality of spokes attached to the hub component, the spokes being configured to extend radially outward from the hub component and close radially inward over one or more cords of chordae tendineae of a heart to thereby secure the one or more cords in proximity to the hub component.

In certain embodiments, the hub is disc-shaped. Alternatively, the hub component may have a cylindrical shape. The plurality of spokes may comprise first and second spokes that are offset from one another with respect to a longitudinal axis of the hub component. In certain embodiments, the hub component comprises a spool, wherein the plurality of spokes are configured to be at least partially wrapped around the spool. The plurality of spokes may consist of two spokes. The plurality of spokes may consist of four spokes. The plurality of spokes may comprise memory metal. In certain embodiments, the chordae tendineae capturing device is configured to be introduced into a heart ventricle using a catheter delivery system and to be detached from the catheter delivery system in an implanted state.

In some implementations, the present disclosure relates to a method for treating a heart valve. The method comprises introducing a catheter delivery system into a ventricle of a heart, positioning the catheter delivery system at a level of chordae tendineae disposed in the ventricle, the chordae tendineae connecting papillary muscles to respective leaflets of an atrioventricular valve associated with the ventricle, advancing a guide wire from the catheter delivery system around the chordae tendineae and into proximity with the catheter delivery system, thereby trapping at least a portion of the chordae tendineae within the guide wire, advancing a chordae tendineae snare device from the catheter delivery system over the guide wire, the chordae tendineae snare device forming a horseshoe-shaped form around the at least a portion of the chordae tendineae, thereby causing the chordae tendineae to converge toward a central flow axis of the atrioventricular valve, and withdrawing the catheter delivery system from the ventricle.

The method may further comprise, after advancing the guide wire and before advancing the chordae tendineae snare device, exchanging the guide wire for a wire that is relatively stiffer than the guide wire. The method may further comprise, after advancing the guide wire and before advancing the chordae tendineae snare device, advancing an introducer sheath over the guide wire.

In certain embodiments, the chordae tendineae snare device is 1-2 cm in diameter. In certain embodiments, the chordae tendineae snare device is 2-4 cm in diameter. The chordae tendineae snare device may comprise a flexible catheter and a memory metal strut that is pre-shaped to form a horseshoe shape at a body temperature. In certain embodiments, advancing the chordae tendineae snare device over the guide wire is performed at least in part by advancing a pusher device from the catheter delivery system.

The method may comprise, after advancing the chordae tendineae snare device but before said withdrawing the catheter delivery system, determining whether performance of the heart valve is satisfactory. When it is determined that the performance of the heart valve is not satisfactory, the method may comprise at least partially withdrawing the chordae tendineae snare device into the catheter delivery system. In certain embodiments, the method comprises, after advancing the chordae tendineae snare device but before withdrawing the catheter delivery system, determining whether a position of the chordae tendineae is satisfactory. When it is determined that the position of the chordae tendineae is not satisfactory, the method may comprise at least partially withdrawing the chordae tendineae snare device into the catheter delivery system.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 10 provides a flow diagram representing a process for capturing chordae tendineae according to one or more embodiments disclosed herein.

FIG. 11 shows examples of various stages of the process for capturing chordae tendineae as shown in FIG. 10 implemented in a heart according to one or more embodiments.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, with respect to any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or apparatuses/devices described herein may be embodied as integrated components or as separate components. For purposes of comparing various embodiments, certain aspects and advantages of these embodiments are described.

Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Similar reference numbers may be used with respect to separate diagrams and/or embodiments; use of such similar, or identical, reference numbers should not be interpreted as necessarily identifying identical components, and may refer to separate features.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
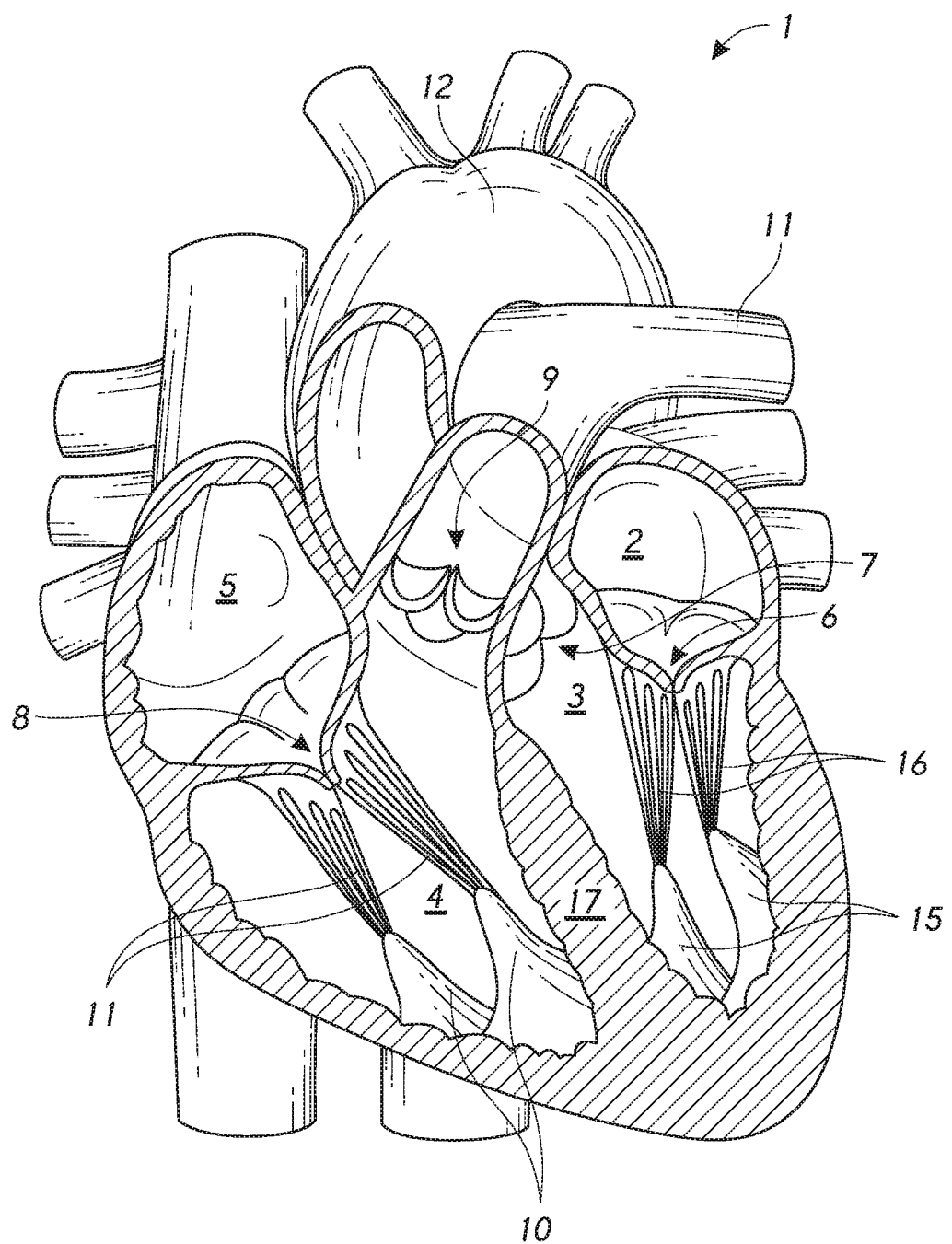
FIG. 1 provides a cross-sectional view of a human heart.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size and position of the leaflets or cusps may be such that when the heart contracts, the resulting increased blood pressure produced within the corresponding heart chamber forces the leaflets at least partially open to allow flow from the heart chamber. As the pressure in the heart chamber subsides, the pressure in the subsequent chamber or blood vessel may become dominant, and press back against the leaflets. As a result, the leaflets/cusps come in apposition to each other such that the leaflets/cusps coapt, thereby closing the flow passage.

The atrioventricular (i.e., mitral 6 and tricuspid 8) heart valves may further comprise a respective collection of chordae tendineae (16, 11) and papillary muscles (15, 10) for securing the leaflets of the respective valves to promote and/or facilitate proper coaptation of the valve leaflets and prevent prolapse thereof. The papillary muscles (15, 10) may generally comprise finger-like projections from the ventricle wall, while the chordae tendineae (16, 10) may comprise cord-like tendons that connect the papillary muscles to the valve leaflets.

With respect to the mitral valve 6, a normal mitral valve may comprise two leaflets (anterior and posterior) and chordae tendineae 16 connecting the leaflets to two corresponding papillary muscles 15. The papillary muscles 15 originate in the left ventricle wall and project into the left ventricle 3. The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure can force the valve to close, while the chordae tendineae 16 may keep the leaflets coapting together and prevent the valve from opening in the wrong direction, thereby preventing blood to flow back to the left atrium 2. The various cords of the chordae tendineae may have different thicknesses, wherein relatively thinner cords are attached to the free leaflet margin, while relatively thicker cords (e.g., strut cords) are attached farther away from the free margin.

With respect to the tricuspid valve 8, a normal tricuspid valve may comprise three leaflets (two shown in FIG. 1) and three corresponding papillary muscles 10 (two shown in FIG. 1). The leaflets of the tricuspid valve 8 may be referred to as the anterior, posterior and septal leaflets, respectively. The valve leaflets are connected to the papillary muscles by the chordae tendineae 11, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle binding and/or adjustment disclosed herein are applicable to atrioventricular valves having any number of leaflets and/or chordae tendineae or papillary muscles associated therewith. The right ventricular papillary muscles 10 originate in the right ventricle wall, and attach to the anterior, posterior and septal leaflets of the tricuspid valve, respectively, via the chordae tendineae 11. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

Figure 2:
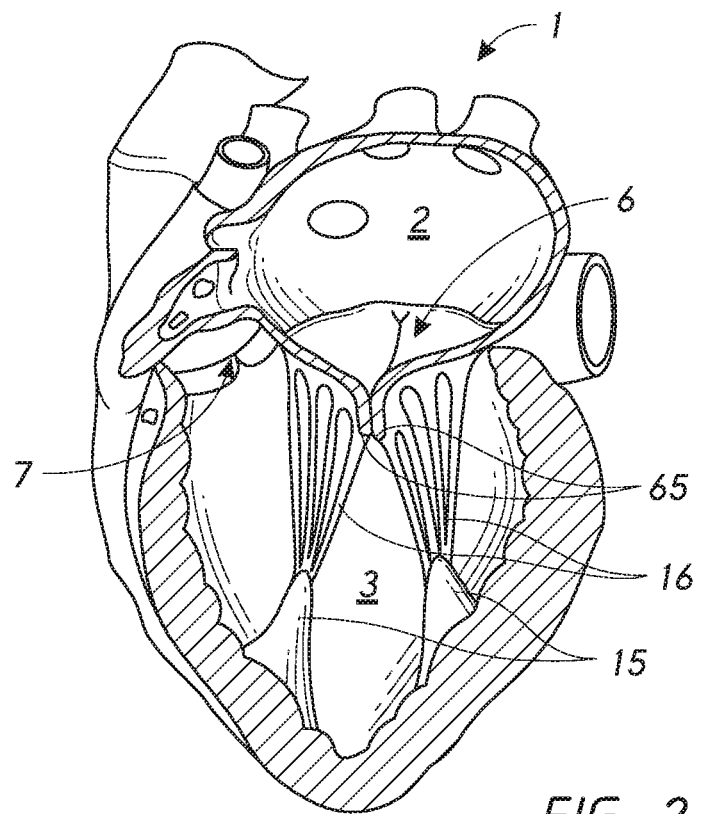
FIG. 2 provides a cross-sectional view of the left ventricle and left atrium of an example heart.

FIG. 2 provides a cross-sectional view of the left ventricle 3 and left atrium 2 of an example heart 1. The diagram of FIG. 2 shows the mitral valve 6, wherein the disposition of the valve 6, papillary muscles 15 and/or chordae tendineae 16 may be illustrative as providing for proper co-apting of the valve leaflets 65 to advantageously at least partially prevent regurgitation and/or undesirable flow into the left atrium from the left ventricle 3 and vice versa. Although a mitral valve 6 is shown in FIG. 2 and various other figures provided herewith, and described herein in the context of certain embodiments of the present disclosure, it should be understood that chordae tendineae capture and/or adjustment principles disclosed herein may be applicable with respect to any atrioventricular valve and associated anatomy (e.g., chordae tendineae, papillary muscles, ventricle wall, etc.), such as the tricuspid valve.

As described above, with respect to a healthy heart valve as shown in FIG. 2, the valve leaflets 65 may extend inward from the valve annulus and come together in the flow orifice to permit flow in the outflow direction (e.g., the downward direction in FIG. 2) and prevent backflow or regurgitation toward the inflow direction (e.g., the upward direction in FIG. 2). For example, during atrial systole, blood flows from the atria 2 to the ventricle 3 down the pressure gradient, resulting in the chordae tendineae 16 being relaxed due to the atrioventricular valve 6 being forced open. When the ventricle 3 contracts during ventricular systole, the increased blood pressures in both chambers may push the valve 6 closed, preventing backflow of blood into the atria 2. Due to the lower blood pressure in the atria compared to the ventricles, the valve leaflets may tend to be drawn toward the atria. The chordae tendineae 16 can serve to tether the leaflets and hold them in a closed position when they become tense during ventricular systole. The papillary muscles 15 provide structures in the ventricles for securing the chordae tendineae 16 and therefore allowing the chordae tendineae 16 to hold the leaflets 65 in a closed position. The papillary muscles 15 may include an anterolateral papillary muscle, which may be tethered to the posterior leaflet, for example, and a posteromedial papillary muscle, which may be tethered to the anterior leaflet, for example. With respect to the state of the heart 1 shown in FIG. 2, the proper coaptation of the valve leaflets, which may be due in part to proper position and/or tension of the chordae tendineae 16, may advantageously result in mitral valve operation substantially free of leakage.

Heart valve disease represents a condition in which one or more of the valves of the heart fails to function properly. Diseased heart valves may be categorized as stenotic, wherein the valve does not open sufficiently to allow adequate forward flow of blood through the valve, and/or incompetent, wherein the valve does not close completely, causing excessive backward flow of blood through the valve when the valve is in a closed state. In certain conditions, valve disease can be severely debilitating and even fatal if left insufficiently treated. With regard to incompetent heart valves, over time and/or due to various physiological conditions, the position and/or tension of the chordae tendineae and/or papillary muscles may become altered, thereby pulling the valve leaflets at least partly open, which may cause valve regurgitation. For example, functional mitral valve regurgitation can occur when the left ventricle of the heart is distorted or dilated, displacing the papillary muscles, and chordae tendineae attached thereto, that support the mitral valve leaflets. For example, the valve leaflets may no longer come together to close the annulus, thereby resulting in blood flow back into the atrium. If left untreated, functional mitral valve regurgitation can overload the heart and can lead to or accelerate heart failure. Moving or pulling the chordae tendineae closer to the flow axis of the valve annulus according to their natural and healthy positions can potentially reduce occurrence of valve regurgitation.

Figure 3:
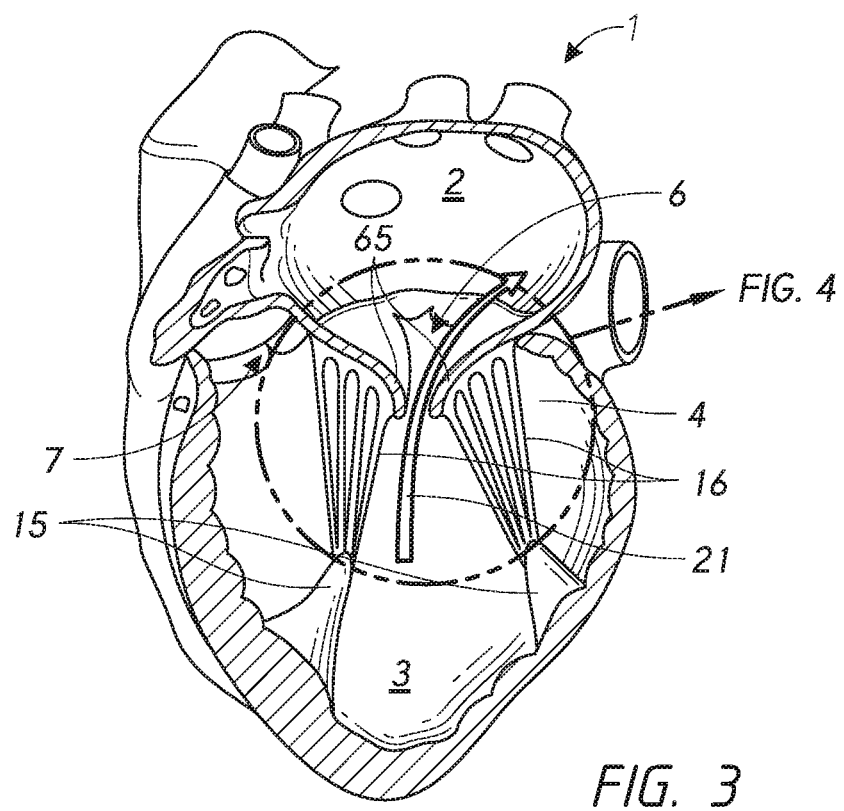
FIG. 3 provides a cross-sectional view of a heart experiencing mitral regurgitation.

FIG. 3 illustrates a cross-sectional view of a heart 1 experiencing functional mitral valve regurgitation flow 21, which may be caused at least in part by dilation of the left ventricle. Left ventricle dilation can cause changes in the position of the papillary muscles 15, thereby allowing the flow 21 back from the ventricle 3 to the atrium 2. Dilation of the left ventricle can be causes by any number of conditions, such as focal myocardial infarction, global ischemia of the myocardial tissue, or idiopathic dilated cardiomyopathy, resulting in alterations in the geometric relationship between papillary muscles and other components associated with the valve(s) that can cause valve regurgitation. Functional regurgitation may further be present even where the valve components may be normal pathologically, yet may be unable to function properly due to changes in the surrounding environment. Examples of such changes include geometric alterations of one or more heart chambers and/or decreases in myocardial contractility. In any case, the resultant volume overload that may exist as a result of an insufficient valve may increase chamber wall stress, eventually resulting in a dilatory effect that causes papillary muscle and/or chordae tendineae alteration resulting in valve dysfunction and degraded cardiac efficiency.

When the chordae tendineae 16 are pulled away from the flow axis of the valve 6, the attached valve leaflets 65 may no longer come together sufficiently to close the annulus and prevent blood flow back into the atrium 2. Solutions presented herein provide devices and methods for bringing the chordae tendineae 16 closer to their previous position, which may advantageously reduce the occurrence of mitral regurgitation. As shown in FIG. 3, the failure of the leaflets 65 of the mitral valve (or tricuspid valve) to come into a state of coaptation can result in an opening between the mitral valve leaflets 65 during the systolic phase of the cardiac cycle, which allows the leakage flow 21 of fluid back up into the atrium 2. In addition to the unwanted flow 21 in the outflow direction (e.g., the upward direction in FIG. 3), the failure of the valve leaflets 65 to coapt properly may result in unwanted backflow or regurgitation toward the inflow direction (e.g., the downward direction in FIG. 3) as well in certain conditions.

Various techniques that suffer from certain drawbacks may be implemented for treating mitral valve dysfunction, including surgical repair or replacement of the diseased valve or medical management of the patient, which may be appropriate/effective primarily in early stages of valve dysfunction, during which levels of regurgitation may be relatively low. For example, such medical management may generally focus on volume reductions, such as diuresis or afterload reducers, such as vasodilators, for example. Valve replacement operations may also be used to treat regurgitation from valve dysfunction. However, such operations can result in ventricular dysfunction or failure following surgery. Further limitations to valve replacement solutions may include the potential need for prolonged or lifelong therapy with powerful anticoagulants in order to mitigate the thromboembolic potential of prosthetic valve implants. Moreover, in the case of biologically-derived devices, such as those used as mitral valve replacements, the long-term durability may be limited. Another commonly employed repair technique involves the use of annuloplasty rings to improve mitral valve function. An annuloplasty ring may be placed in the valve annulus and the tissue of the annulus sewn or otherwise secured to the ring. Annuloplasty rings can provide a reduction in the annular circumference and/or an increase in the leaflet coaptation area. However, annuloplasty rings may flatten the saddle-like shape of the valve and/or hinder the natural contraction of the valve annulus. In addition, various surgical techniques may be used to treat valve dysfunction. However, such techniques may suffer from various limitations, such as requiring opening the heart to gain direct access to the valve and the valve annulus. Therefore, cardiopulmonary bypass may be required, which may introduce increased morbidity and mortality to the surgical procedures. Additionally, for surgical procedures, it can be difficult or impossible to evaluate the efficacy of the repair prior to the conclusion of the operation.

Various solutions disclosed herein relate to devices and methods for treating valve dysfunction without the need for cardiopulmonary bypass and without requiring major remodeling of the dysfunctional valve, such as through the use of passive techniques to capture and adjust some or all of the chordae tendineae to alter the degree and/or direction of pull of the cord(s) of the chordae tendineae on corresponding leaflets of the associated heart valve are disclosed for reducing regurgitation while maintaining substantially normal leaflet anatomy. Further, various embodiments disclosed herein provide for the treatment of valve dysfunction that can be executed on a beating heart, thereby allowing for the ability to assess the efficacy of the papillary muscle re-positioning treatment and potentially implement modification thereto without the need for bypass support.

Certain embodiments disclosed herein provide solutions for incompetent heart valves that involve using an implanted capture device for capturing one or more cords of the chordae tendineae in order to adjust the cord(s) and pull the cord(s) in an inward direction with respect to a flow axis of the valve. The term "cord" is used herein according to its broad and ordinary meaning and may be understood in the context of chordae tendineae to refer to one or more, or all, individual strings, tendons, chordae, or cords/chords of a group of the same that collectively comprise the chordae tendineae associated with a heart valve, or a valve leaflet thereof. The solutions presented herein may be used to at least partially change the position of one or more cords of the chordae tendineae in order to reduce the occurrences and/or severity of regurgitation, such as mitral regurgitation.

Chordae Tendineae Capture/Adjustment

As referenced above, certain embodiments disclosed herein provide for systems, devices and methods for capturing and/or adjusting the position of chordae tendineae (CT) in the left and/or right ventricles of a heart in order to improve valve coaptation during ventricular systole. For example, CT capture/adjustment devices are disclosed that may be implanted independently in one of the ventricles of the heart. Such devices may be introduced into the patient system through surgical or, advantageously, minimally-invasive means.

Figure 4:
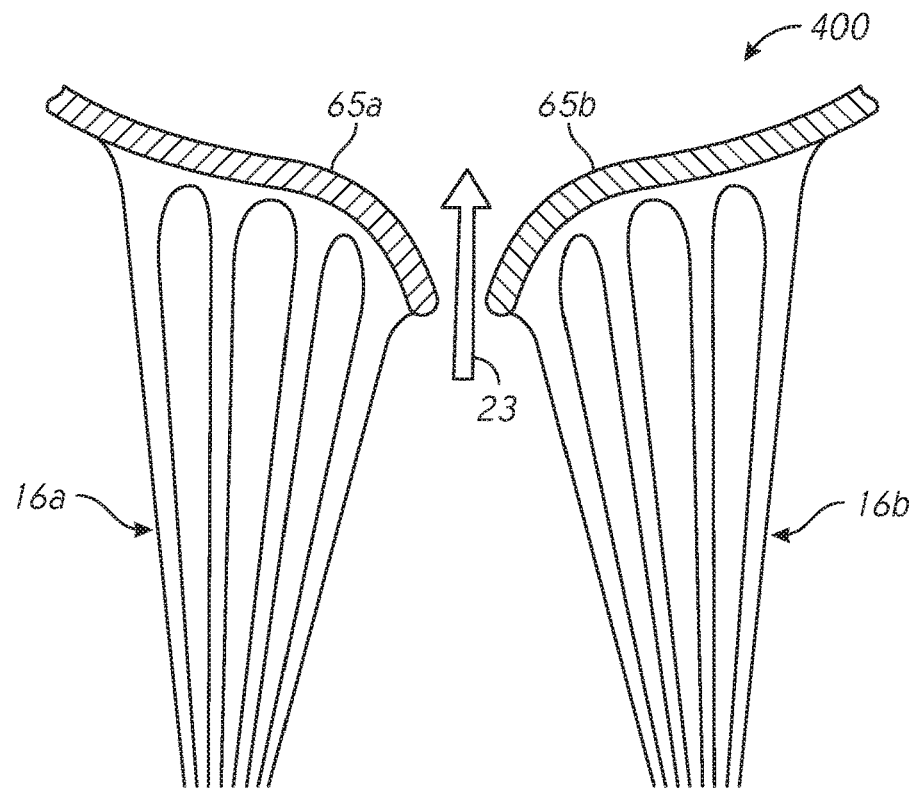
FIG. 4 illustrates a portion of the heart shown in FIG. 3.

FIG. 4 illustrates a portion of the heart 1 shown in FIG. 3 and described above. In particular, FIG. 4 shows valve leaflets 65a, 65b in a closed state, wherein undesirable tension and/or outward pull exerted on the leaflets by respective chordae tendineae results in an opening 23 through which fluid may flow in a backflow direction. As shown, the CT 16a, 16b may tether the leaflets 65a, 65b in a position such that the edges of the leaflets do not come into proper coaptation during ventricular systole. With the CT 16a, 16b in a position to exert outward pull on the leaflets 65a, 65b that prevents proper coaptation, regurgitation may be present.

Figure 5:
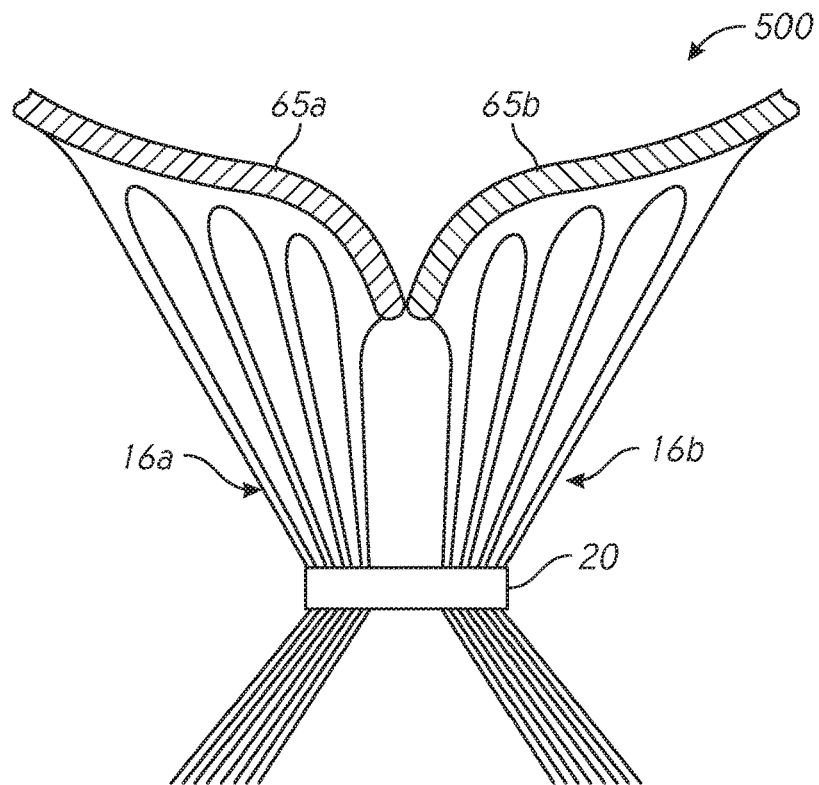
FIG. 5 shows a portion of a heart valve having a chordae tendineae capture device implemented therein according to one more embodiments.

Chordae tendineae capturing methods and/or devices disclosed herein may include structure for corralling and/or drawing-in one or more cords to provide advantageous repositioning of the CT. Various solutions for capturing and/or repositioning chordae tendineae to allow for proper closing of the associated valve during ventricular systole may be understood with reference to FIG. 5. FIG. 5 shows a heart valve 500 including valve leaflets 65a, 65b coupled to respective chordae tendineae (CT) 16a, 16b, wherein the CT are at least partially captured by a CT capture device 20. The device 20 may be implemented to treat, for example, mitral regurgitation. In certain embodiments, implantation of the device 20 provides for remodeling of the valve (e.g., mitral valve) by effecting convergence of one or more cords of the CT 16a, 16b towards a central axis or point within the heart ventricle. The leaflets 65a, 65b of the valve may thus be pulled more closely together, which may advantageously result in an improvement of function and/or reduction of regurgitation through improved leaflet coaptation.

The device 20 may comprise any suitable or desirable form, shape, or configuration, and may comprise any number of parts or components. For example, disclosed herein are embodiments of the device 20 comprising one or more hubs, spokes, bands, wires, forms, or the like. Procedures and methods for implanting CT capture devices in accordance with the present disclosure may involve transcatheter delivery, such as transfemoral, transseptal, transapical, or other type of transcatheter procedure.

Figure 6:
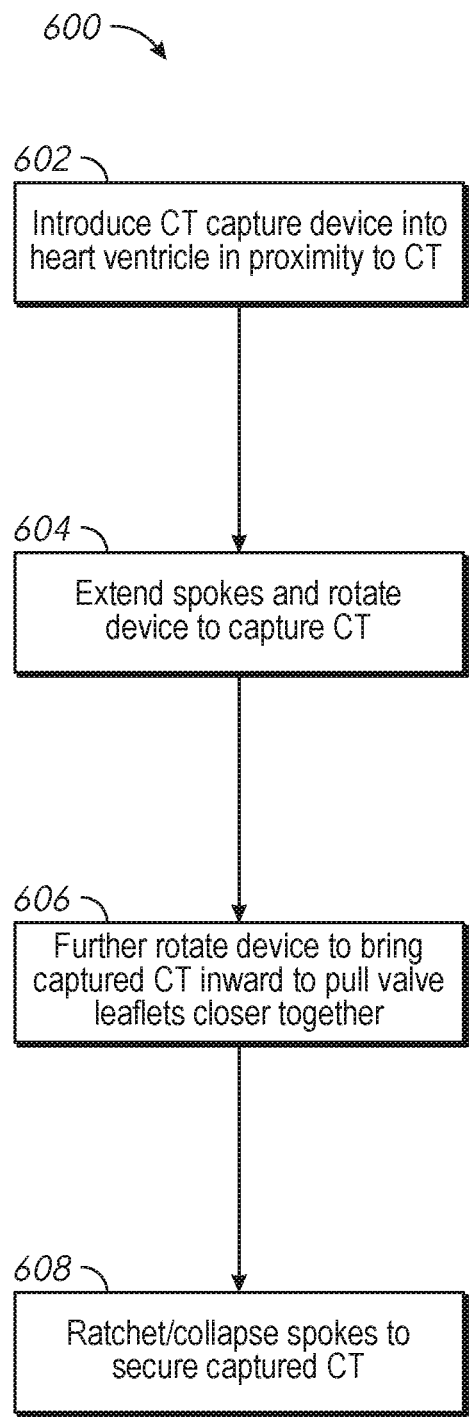
FIG. 6 provides a flow diagram representing a process for capturing chordae tendineae according to one or more embodiments disclosed herein.
Figure 7:
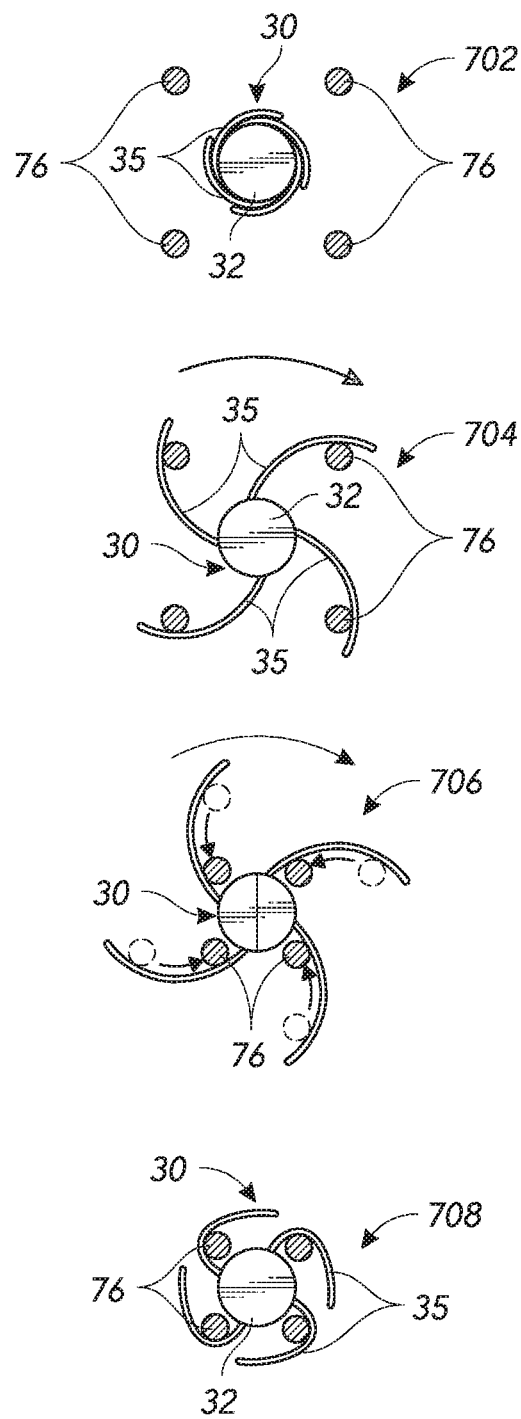
FIG. 7 shows examples of various stages of the process for capturing chordae tendineae as shown in FIG. 6 implemented in a heart according to one or more embodiments.

FIG. 6 provides a flow diagram representing a process for capturing chordae tendineae (CT) using a CT capture device 30 according to one or more embodiments disclosed herein. FIG. 7 shows examples of various stages of the process for capturing chordae tendineae as shown in FIG. 6.

At block 602, the process 600 involves introducing the CT capture device 30 into a ventricle of a heart in proximity to chordae tendineae thereof. For example, the stage 702 shows a top-down view of a CT capture device 30 disposed in proximity to a plurality of cords 76 of chordae tendineae in the relevant heart ventricle. Although a certain number and configuration of cords is illustrated, as well as a certain positioning of the CT capture device 30, it should be understood that the process 600 may be implemented in connection with any number or configuration of cords and/or any positioning of a CT capture device within a proximity that may be effective for capturing one or more cords by the CT capture device.

In certain embodiments, prior to full deployment, the device 30 may take the form a relatively small disc or hub component 32 having one or more spokes 35 or extensions that may be configured to radiate or extend outward from the central hub, such as through rotation or other activation of the hub 32 and/or spokes 35. When initially disposed in proximity to the cords 76, the spokes 35 may be in a retracted state, such as wrapped at least partially around the central hub 32. The hub may be disc-shaped, cylindrical, spherical, elliptical, or otherwise-shaped. Furthermore, the hub 32 may comprise a spool or other form or component around which the spokes 35 may be at least partially wound. In certain embodiments, the shape of the CT capture device 30 may be at least partially similar in certain respects to the shape is of a spiral galaxy, such as the Milky Way.

In certain embodiments, the spokes 35 may comprise wire, such as memory metal wire (e.g., Nitinol). The spokes 35 may be designed to at least partially close concentrically around themselves during deployment, wrapping around the central hub. The device 30 may be configured to be at least partially collapsible into, for example, a cylindrical-type shape. In a collapsed/retracted state, the device 30 may be suitable for introduction through a guiding catheter and/or introducer sheath.

At block 604, the process 600 involves extending the spokes/extensions 35 and rotating the device 30 by some amount such that one or more of the spokes/extensions 35 come in contact with and/or capture or catch one or more cords 76 of chordae tendineae, as shown at stage 704. It should be appreciated that although four spokes 35 are shown for illustration purposes, CT capture devices in accordance with embodiments of the present disclosure may have any suitable or desirable number of spokes or extensions and may be configured to capture any number of cords. Once extended, the process 600 may involve capturing or contacting one or more cords 76 using one or more of the spokes 35 by rotating the device 30 in a first direction (e.g., clockwise with respect to a top-down view, as shown) or an opposite direction (e.g., counterclockwise).

As shown at stage 704, one or more of the spokes 35 may contact or catch one or more cords 76 at or near a distal end portion of the spoke initially. The spokes 35 may have an at least partially curved shape, as illustrated, such that rotation of the device 30 in a direction of concavity of the spoke(s) 35 may serve to draw the captured cords 76 in an inward direction towards the central hub 32. Although the diagrams of FIG. 7 illustrate each of the spokes of the device 30 as capturing or catching one cord, it should be understood that the process 600 may involve catching/capturing more than one cord, or no cords, with any given spoke of the device 30.

At block 606, the process 600 involves further rotating the device 30 to bring the captured cords inward to thereby advantageously pull the associated valve leaflets closer together to reduce regurgitation or otherwise improve valve function. As referenced above, the concavity or other feature (s) of the spokes 35 may cause the captured cords 76 to be pulled inward toward the central hub 32.

At block 608, the process 600 may involve ratcheting or otherwise collapsing, at least partially, the spokes 35 around or towards the central hub 32 to secure the captured cords 76 in the desired position. In certain embodiments, the central hub 32 of the CT capture device 30 may serve as an anchor point for the spokes, and may further comprise a ratchet mechanism for ratcheting the spokes as shown. The device 30 may further comprise a means or mechanism for attachment to and/or detachment from the delivery system used to deliver the device 30 to the position(s) shown in FIG. 7. For example, the ratchet mechanism may serve to constrain the spokes 35 in their fully open configuration (e.g., spiral configuration) prior to final deployment of the device. With regard to embodiments comprising memory metal wire spokes, the spokes may be under tension in the extended position; as the ratchet mechanism is activated, the spokes may return (e.g., gradually) to their pre-formed memory position. For example, the memory position of the spokes may be in a position similar to that shown at stage 702, wherein the spokes 35 are wrapped round the hub 32 in a wound spiral configuration.

In certain embodiments, the capturing of the cords 76 shown in FIG. 7 and described in connection with the process 600 of FIG. 6 may be at least partially reversible. For example, the process 600 and/or configuration of the device 30 and/or associated delivery system may allow for the spokes 35 to open and close, thereby allowing for repositioning and/or removal of the device 30 prior to final deployment, or even retrieval and/or repositioning of the device after final deployment.

Stage 708 shows the CT capture device 30 in a final deployed state, wherein the captured cords 76 are constrained by the folded, or retracted, spokes 35. The degree to which the spokes are ratcheted or tightened around the captured CT may be determined by the resulting movement of the CT and/or reduction in regurgitation of the associated valve. In its fully deployed state, the device 30 may remain in place inside the heart ventricle (e.g., left ventricle) indefinitely to provide on-going improvement of valve functioning. In certain embodiments, the deployed device 30 and/or central hub 32 thereof may have a shape or form resembling at least in part a button or similar form.

Figure 8:
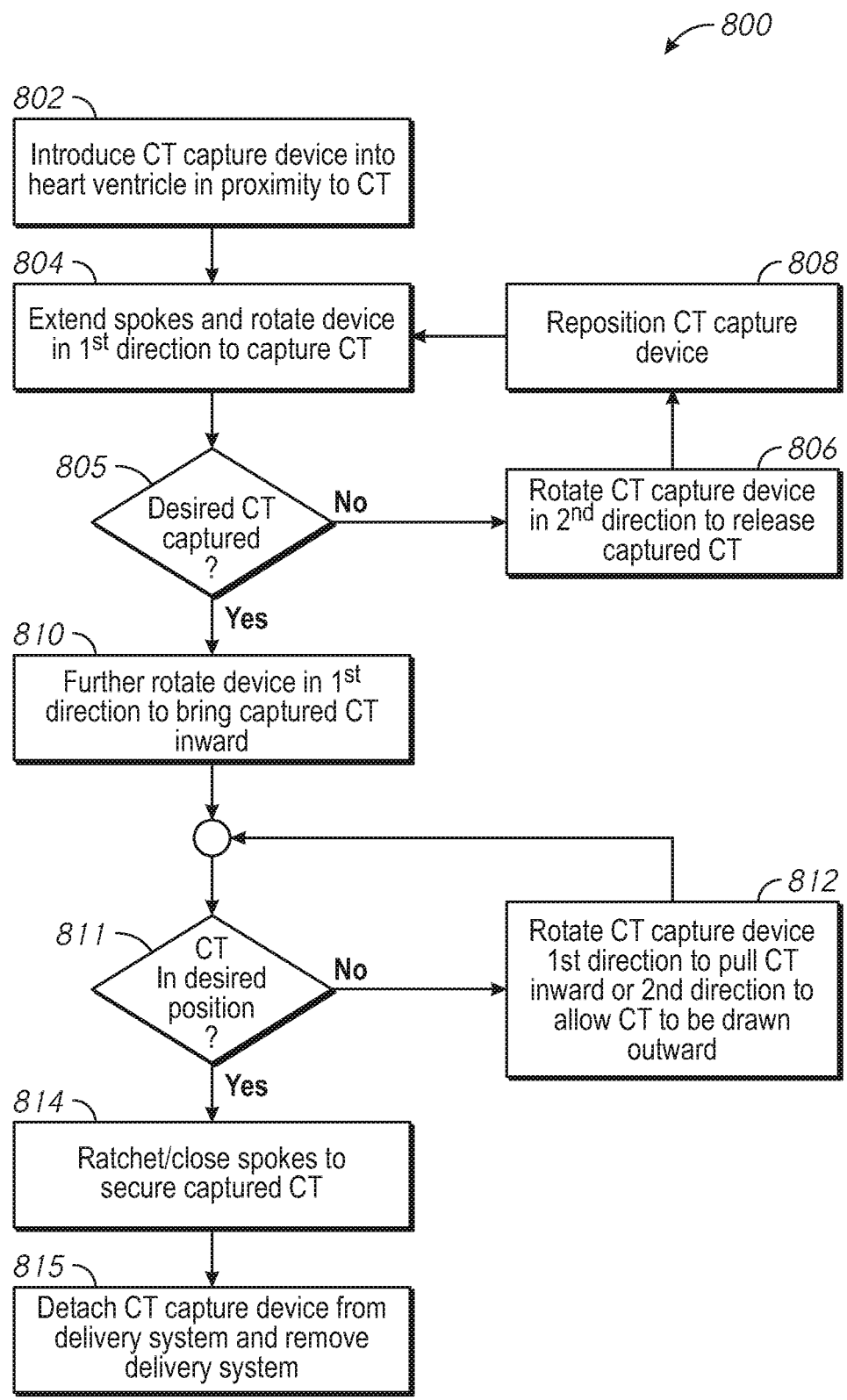
FIG. 8 is a flow diagram for a process for adjusting chordae tendineae position according to one or more embodiments.

FIG. 8 is a flow diagram for a process for adjusting chordae tendineae position according to one or more embodiments. At block 802, the process 800 involves introducing a chordae tendineae (CT) capture device into a ventricle of a heart and positioning the CT capture device in proximity to one or more cords of chordae tendineae disposed in the ventricle and attached to an atrioventricular valve thereof. The CT capture device may be introduced into the heart ventricle using a transcatheter procedure, such as a transfemoral, transapical, transseptal, or other transcatheter procedure. In certain implementations, the process 800 may involve introducing the CT capture device into the heart ventricle during open heart surgery, or using a hybrid surgical/transcatheter method. The CT capture device may be introduced into the desired position using an introducer sheath containing the device, which may be advanced into, for example, the left ventricle.

In certain embodiments, the CT capture device is positioned below the relevant atrioventricular valve (e.g., mitral valve) and at least partially above the papillary muscles, at or around the level of the chordae tendineae attached to the valve. The sheath may be withdrawn, or the CT capture device may be otherwise exposed. In certain embodiments, the CT capture device may include one or more spokes or extensions, such as spiral-shaped spokes, or the like.

At block 804, the process 800 involves extending the one or more spokes or extensions of the CT capture device. For example, the spokes may be deployed in a plane parallel, or substantially parallel, to the valve annulus. The delivery system used to position the CT capture device may be disposed in a position about parallel with the CT and perpendicular to the deployment plane of the spokes.

As further shown at block 804, the process 800 involves rotating the CT capture device in a first direction in order to contact and/or capture one or more cords of the CT. Rotation of the device may bring one or more of the spokes in contact with one or more cords, wherein a shape or configuration of the spoke(s) may facilitate capturing of the cords when contacted and further rotated. For example, the spokes may utilize a concave shape that causes cords that contact the spoke(s) to be draw inward when the CT capture device is rotated in the direction of concavity.

At decision block 805, the process 800 may involve determining whether the previously-implemented steps have resulted in the desired capture of CT. For example, it may be determined whether the desired cords or number of cords have been captured, and/or whether the desired spoke(s) have captured chord(s). In certain embodiments, assessment of CT capture may be made using echocardiography or other means.

If it is determined that the desired CT capturing has not been achieved, the process 800 may involve, at block 806, rotating the CT capture device in a second direction, which may be in an opposite direction to the first direction. Rotation in the second direction may at least partially release the spoke(s) from captured CT to allow for adjustment/reposition of the CT capture device, as shown at block 808. In certain embodiments, rotation in the second direction may release all of the captured CT. In certain implementations, if a satisfactory result is not achieved as determined at block 805, the CT capture device may be fully retrieved at this stage by withdrawing the CT capture device into the introducer sheath. Where it is desirable to reposition the CT device at block 808, the device can be repositioned, and the process of capturing CT can be repeated starting back at block 804.

If the desired capture is achieved at block 805, the process 800 may proceed to block 810, where the CT capture device may be further rotated in the first direction in order to bring the captured CT in an inward direction. In certain embodiments, upon continuing rotation, the spiral/concave-shaped spokes of the CT capture device operate to force the caught cords to move closer to a central hub or portion of the device, which may in turn pull the valve leaflets closer together via the attachment of the CT to respective valve leaflets.

At decision block 811, the process 800 involves determining whether the previous steps have resulted in a desired repositioning of the CT. For example, evaluation may be made whether the CT device and CT are in a desired position and/or whether the resulting function of the heart valve is satisfactory. Assessment at block 811 may be made using echocardiography or other means. Whether the results evaluated at block 811 are satisfactory may be determined by the resulting movement of the CT and/or reduction in regurgitation for the valve. For example, valve function may be evaluated to determine whether acceptable closing of the valve is achieved. If not, the process 800 may proceed to block 812, where the CT capture device may be rotated further in the first direction to further tighten or bring inward the captured CT, or alternatively, the CT capture device may be rotated in the second direction opposite the first direction to release or loosen the CT. The purpose of the step of block 812 may be to achieve the desired capture of the CT, and therefore the modification step(s) implemented at block 812 may be directed by the particular modification/repositioning desired. Blocks 811 and 812 may provide a loop for adaptively producing the desired result through evaluation and subsequent adjustment until the desired result is achieved.

The results of the configuration/adjustment of the CT capture device may be observed continuously or at selected intervals to determine when the CT have been repositioned sufficiently to provide a desired improvement in closure of the valve during the phase of the cardiac cycle associated with closure of the relevant valve (e.g., during systole in the case of a mitral valve). Therefore, the process 800 and/or other processes, devices and systems disclosed herein may advantageously provide a tunable CT adjustment system, which may be tuned while monitoring the effect of the system, such as through the use of echo or other visualization guidance. In certain embodiments, if a satisfactory result is not achieved at block 811, the process 800 may involve fully retrieving the CT capture device by withdrawing into the introducer sheath.

At block 814, if a satisfactory result has been achieved as demonstrated at block 811, the process 800 involves ratcheting or closing the spokes of the CT capture device to at least partially secure the captured CT in the desired position. For example, the CT capture device and/or delivery system associated therewith may comprise a ratchet system, which may be configured to cause the spokes of the CT capture device to at least partially wrap around the central hub or portion of the device, thus keeping the caught cords in proximity to the central hub or portion. It should be understood that any of the steps of the process 800 may be reversible in certain embodiments.

At block 815, the process 800 may involve detaching or otherwise disassociating the CT capture device from the delivery system to leave the final implant as configured in the heart ventricle.

Figure 9:
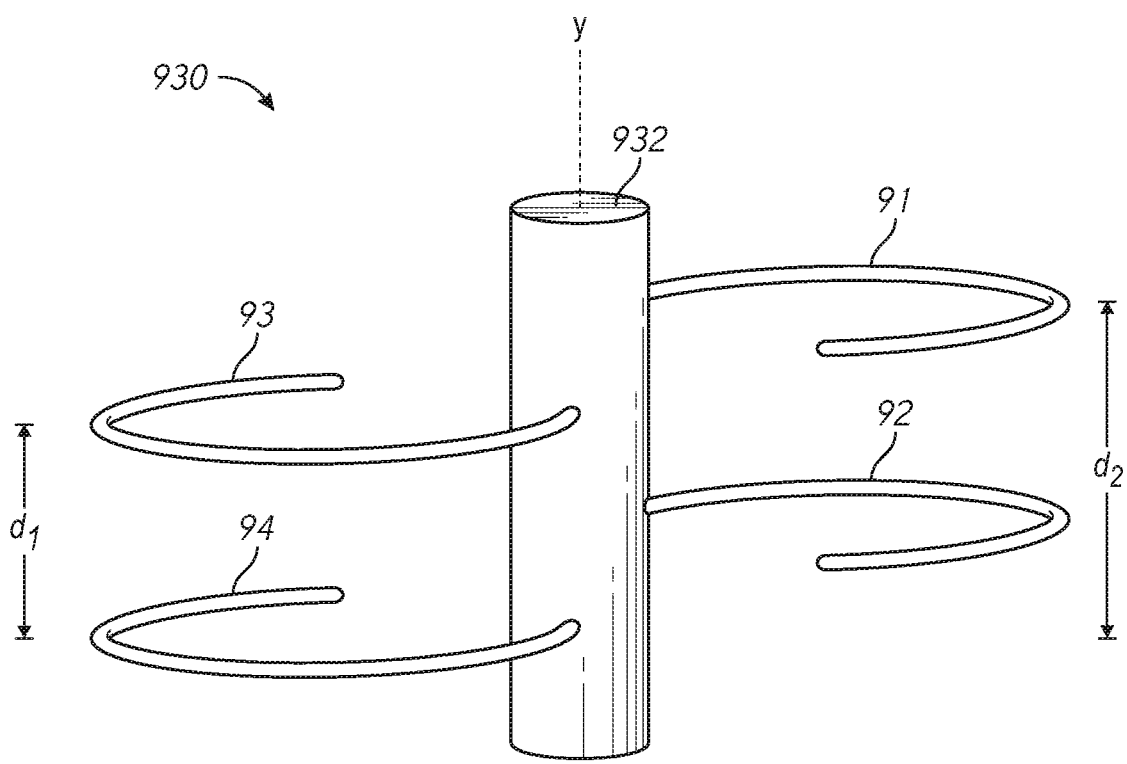
FIG. 9 is a perspective view of a chordae tendineae capture device according to one or more embodiments.

FIG. 9 provides a perspective view of a chordae tendineae (CT) capture device 930 according to one or more embodiments. The device 930 includes a central hub portion 932, which may be generally cylindrical in shape, as shown. The device 930 may comprise a plurality of spokes or extensions 91-94, which may be vertically staggered in some embodiments. For example, one or more of the spokes (e.g., spokes 91, 93) may be offset vertically along a longitudinal axis y of the cylindrical hub 932 of the device 930. In certain embodiments two or more spokes may be disposed at a first vertical position, while two or more other spokes are disposed at a second vertical position offset from the first vertical position. The vertical staggering/offsetting of the spokes may allow for the device 930 to be more easily loaded into a relatively small-sized introducer or catheter. The device 930 may be implanted in a ventricle of a heart according to any process or operation disclosed herein.

Chordae Tendineae Snare

Devices and methods for capturing and/or adjusting chordae tendineae (CT) in accordance with the present disclosure may utilize devices having any suitable or desirable form. Certain embodiments disclosed herein provide for the capture of CT using a snare or similar device. In certain embodiments, a snare may be at least partially wrapped around the CT in a heart ventricle to force or push the CT to converge toward a central point in order to improve mitral leaflet coaptation. For example, the central point may be aligned with or proximate to a flow axis of a heart valve associated with the wrapped CT.

FIG. 10 provides a flow diagram representing a process 1000 for capturing chordae tendineae according to one or more embodiments disclosed herein. FIG. 11 shows examples of various stages of the process 1000 for capturing chordae tendineae as shown in FIG. 10.

The process 1000 may involve, at block 1002, inserting a catheter 40 into a heart ventricle using a transcatheter procedure. The catheter 40 may be inserted as part of a delivery system for a CT snare device, wherein the catheter is capable of holding the CT snare device and/or a guiding catheter. The system may be introduced via a transapical, transseptal or possibly transfemoral approach. In certain embodiments, the delivery system may be advanced via the apex into the left ventricle. The distal end of the catheter 40 may provide the working end of the delivery system, and may be brought into proximity with the CT 16, such as at or just below the level of the CT.

At block 1004, the process 1004 involves advancing a guide wire 53 from the catheter 40, and further advancing the CT snare device 50 from the catheter 40 to form a partial loop around the CT 16. For example, a specially-curved catheter and guide wire 53 may be advanced out of the delivery system. The wire 53 and catheter may be shaped to allow them to follow a curve around the interior wall of the ventricle. The wire 53 may be curved around the CT 16 in a plane roughly parallel to the valve annulus (not shown) of the valve 13 and/or at the level of the CT 16. The catheter and wire may further be advanced and manipulated around a curve until it has completed a near circle around the wall of the ventricle, forming an at least partial loop and terminating proximal to the delivery system. Several cords of the CT 16 may advantageously be captured within the loop.

The end of the wire 53 may be caught and pulled out of the system, resulting in a through and through wire that loops round the outside of several cords, with both ends of the wire outside the delivery system and in proximity to the operator. In certain embodiments, the wire 53 may be exchanged for a stiffer wire, such as through the use of an exchange catheter, to facilitate the advancement of one or more components over the wire 53. For example, an introducer sheath may be advanced over the wire, coaxial with the delivery system, until it has passed the CT. In certain embodiments, the guide wire may further be exchanged for a floppy wire.

Once the guide wire 53 has been looped around the CT 16, the snare device 50 may be advanced from the catheter 40 into the ventricle, such as from another lumen of the delivery system. The device 50 may take the form of a relatively short horseshoe-shaped, or broken-hoop-shaped, tube. In certain embodiments, the snare device 50 may be approximately 1-2 cm in diameter, or may be approximately 2-4 cm in diameter. The snare device 50 may comprise material rigid enough to constrain the CT 16 inside the loop, yet flexible enough to be advanced in a relatively straight configuration over the guide wire 53. In certain embodiments, the snare device 50 may be manufactured using a combination of a flexible catheter material, reinforced by a memory metal (e.g. Nitinol) strut that has been pre-shaped to form a horseshoe or hoop configuration when heated to body temperature.

The snare device 50 may be introduced onto the wire 53, inside a guiding catheter, and followed by a pusher component, such as a relatively rigid, straight catheter. The pusher component (not shown) may be advanced until the device 50 is at the level of the CT 16 and disposed in a position to form a relatively tight loop around the CT 16 once deployed. The snare device 30 may be exposed when the pusher component and/or the internal guiding catheter/introducer are withdrawn. Upon withdrawal of the guiding catheter, the snare device 50 may take its final hoop shape and operate to constrain the CT 16, such as in the direction of an imaginary central point. In certain embodiments, the process 1000 may involve assessing performance, position and/or functionality of the snare device 50 with respect to operation of the valve 13 (e.g., mitral valve).

At block 1006, the process 1000 involves forming a loop with the CT snare device. The loop may advantageously be relatively tight to constrain the CT 16 in a position that causes the valve leaflets 65 to come into a position of coaptation. With the snare device 50 position as shown at stage 1106 of FIG. 11, the CT 16 may be trapped from the outside, rather from the inside as in certain other embodiments. If the resulting position and/or valve performance are satisfactory, the CT capture device 50 can be fully deployed at least in part by removing the guide wire 53. If device retrieval is advisable or desirable before deployment, retrieval may be achieved at least in part by re-sheathing the device 50 inside the guiding catheter and withdrawing the device 50. In certain embodiments, retrieval may be possible at substantially any point before removal of the wire.

Chordae Tendineae Adjustment Tunability

Figure 12:
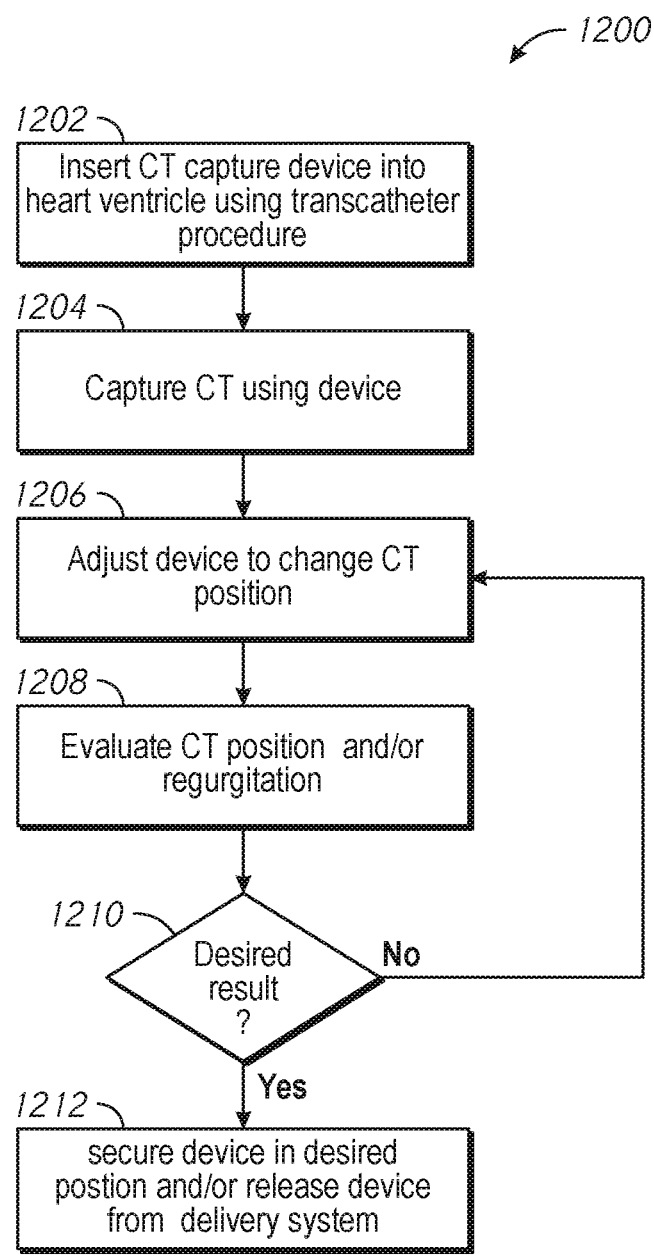
FIG. 12 is a flow diagram for a process for adjusting chordae tendineae position according to one or more embodiments.

FIG. 12 is a flow diagram for a process 1200 for adjusting chordae tendineae (CT) position according to one or more embodiments. At block 1202, the process 1200 involves inserting a CT capture device, such as a hub-and-spoke device or snare device as described in greater detail herein, into a heart ventricle using a transcatheter procedure. Although FIG. 12 describes a transcatheter procedure, in certain embodiments, the CT capture device may be introduced into the heart ventricle using surgical means, such as during an open-heart surgery procedure.

At block 1204, the process 1200 involves using the CT capture device to capture a plurality of cords of CT associated with a heart valve. For example, capturing the cords may involve drawing the cords in some manner inward to allow for the valve leaflets to come into proper coaptation, as described in detail herein. At block 1206, the process 1200 involves tightening, winding, or otherwise adjusting the CT capture device to alter the position of the captured CT.

The degree to which the CT capture device is adjusted at block 1206 may be determined by the resulting movement of the CT and/or reduction in regurgitation caused thereby. At block 1208, the process 1200 involves evaluating CT position and/or valve regurgitation resulting from the capture/adjustment of the CT to determine the effectiveness of the CT capture device, such as by determining whether the evaluated position of the CT and/or regurgitation performance evaluated/observed is satisfactory or desirable.

At decision block 1210, the process 1200 involves determining whether the evaluated CT position and/or regurgitation performance evaluated/observed at block 1208 is satisfactory or desirable. If not, the process 1200 returns to block 1206, where the CT capture device may be further adjusted through the tightening, loosening, and/or repositioning of the CT capture device, to thereby further alter the effect of the device on the CT. In certain embodiments, the operator may use echocardiography or any other suitable means to observe the movement of the valve leaflets, such as in real time. The results of the CT capture device positioning/configuration may be observed continuously or at selected intervals to determine when the CT have been repositioned sufficiently to provide a desired improvement in closure of the valve during the phase of the cardiac cycle associated with closure of the relevant valve (e.g., during systole in the case of a mitral valve). Therefore, the process 1200 and/or other processes, devices and systems disclosed herein may advantageously provide a tunable device, which may be tuned while monitoring the effect of the device, such as through the use of echo or other visualization guidance.

If the desired result is achieved as determined at block 1210, the process 1200 continues to block 1212, where the CT capture device may be secured and/or locked in the desired position and/or released from the delivery system to allow the CT capture device to provide continued CT positioning on an on-going basis to improve heart valve function.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A method for treating a heart valve, said method comprising:
   introducing a catheter delivery system into a ventricle of a heart;
   positioning the catheter delivery system at a level of chordae tendineae disposed in the ventricle, the chordae tendineae connecting papillary muscles to respective leaflets of an atrioventricular valve associated with the ventricle;
   advancing a guide wire from the catheter delivery system around the chordae tendineae and into proximity with the catheter delivery system, thereby trapping at least a portion of the chordae tendineae within the guide wire;
   advancing a chordae tendineae snare device from the catheter delivery system over the guide wire, the chordae tendineae snare device forming a horseshoe-shaped form around the at least a portion of the chordae tendineae, thereby causing the chordae tendineae to converge toward a central flow axis of the atrioventricular valve;

withdrawing the catheter delivery system from the ventricle;

post-operatively maintaining the chordae tendineae snare device around the at least a portion of the chordae tendineae below native heart valve leaflets attached to the chordae tendineae to thereby improve leaflet coaptation for the native heart valve leaflets; and after said advancing the guide wire and before said advancing the chordae tendineae snare device, exchanging the guide wire for a wire that is relatively stiffer than the guide wire.

2. The method of claim 1, further comprising, after said advancing the guide wire and before said advancing the chordae tendineae snare device, advancing an introducer sheath over the guide wire.

3. The method of claim 1, wherein the chordae tendineae snare device is 1-2 cm in diameter.

4. The method of claim 1, wherein the chordae tendineae snare device comprises a flexible catheter and a memory metal strut that is pre-shaped to form a horseshoe shape at a body temperature.

5. The method of claim 1, wherein said advancing the chordae tendineae snare device over the guide wire is performed at least in part by advancing a pusher device from the catheter delivery system.

6. The method of claim 1, further comprising, after said advancing the chordae tendineae snare device and before said withdrawing the catheter delivery system, determining whether coaptation of leaflets of the heart valve has increased.

7. The method of claim 6, further comprising, when it is determined that coaptation of the leaflets of the heart valve has not increased, at least partially withdrawing the chordae tendineae snare device into the catheter delivery system.

8. The method of claim 1, further comprising, after said advancing the chordae tendineae snare device and before said withdrawing the catheter delivery system, determining whether a position of the chordae tendineae has changed.

9. The method of claim 8, further comprising, when it is determined that the position of the chordae tendineae has not changed, at least partially withdrawing the chordae tendineae snare device into the catheter delivery system.

10. The method of claim 1, wherein the chordae tendineae snare device includes a circumferential gap between end portions thereof when maintained post-operatively around the at least a portion of the chordae tendineae.

11. The method of claim 1, wherein the chordae tendineae snare device is pre-shaped to hold a horseshoe configuration post-operatively.

12. The method of claim 1, wherein the chordae tendineae snare device comprises a flexible catheter with pre-shaped memory metal frame.

* * * * *